US011183279B2

(12) United States Patent
Trefethen et al.

(10) Patent No.: US 11,183,279 B2
(45) Date of Patent: Nov. 23, 2021

(54) METHOD AND APPARATUS FOR A TREATMENT TIMELINE USER INTERFACE

(71) Applicant: Topcon Healthcare Solutions, Inc., Oakland, NJ (US)

(72) Inventors: John Thomas Trefethen, Friday Harbor, WA (US); James Alvin Morris, Philadelphia, PA (US); Travis Christopher Ryan, Roseville, CA (US); Junsheng Zhang, Ramsey, NJ (US)

(73) Assignee: Topcon Healthcare Solutions, Inc., Oakland, NJ (US)

( * ) Notice: Subject to any disclaimer, the term of this patent is extended or adjusted under 35 U.S.C. 154(b) by 87 days.

(21) Appl. No.: 16/599,675

(22) Filed: Oct. 11, 2019

(65) Prior Publication Data

US 2020/0135307 A1 Apr. 30, 2020

Related U.S. Application Data

(60) Provisional application No. 62/750,612, filed on Oct. 25, 2018.

(51) Int. Cl.
*G16H 15/00* (2018.01)
*G16H 10/60* (2018.01)
*G06F 3/0482* (2013.01)
*G06F 16/907* (2019.01)
(Continued)

(52) U.S. Cl.
CPC ............ *G16H 10/60* (2018.01); *G06F 3/0482* (2013.01); *G06F 3/04845* (2013.01);
(Continued)

(58) Field of Classification Search
CPC ........ G16H 10/60; G16H 15/00; G16H 20/00; G16H 50/20; G06F 16/907; G06F 16/904; G06F 3/0482; G06F 3/04845
See application file for complete search history.

(56) References Cited

U.S. PATENT DOCUMENTS 8,380,530 B2 * 2/2013 Marshall ................ G16H 50/70
705/2
8,401,870 B2 * 3/2013 Whelchel ............... G06Q 10/06
705/2

(Continued)

FOREIGN PATENT DOCUMENTS

GB 2489096 A 9/2012
WO 2017036867 A1 3/2017

OTHER PUBLICATIONS

International Search Report and Written Opinion dated Jan. 28, 2020, in connection with International Patent Application Serial No. PCT/US2019/057524, 16 pgs.

*Primary Examiner* — Dino Kujundzic
(74) *Attorney, Agent, or Firm* — Chiesa Shahinian & Giantomasi PC

(57) ABSTRACT

A system and method for generating and displaying a treatment timeline user interface includes maintaining a database of patient information. The patient information includes patient identification information and exam data associated with patients. In response to a request for information pertaining to a particular patient, a treatment timeline user interface is generated and displayed based on information associated with the particular patient stored in the database. Input is received requesting modification of the displayed treatment timeline and, in response, the treatment timeline is updated and displayed.

17 Claims, 9 Drawing Sheets

(51) Int. Cl.
*G06F 16/904* (2019.01)
*G06F 3/0484* (2013.01)
*G16H 20/00* (2018.01)

(52) U.S. Cl.
CPC .......... *G06F 16/904* (2019.01); *G06F 16/907* (2019.01); *G16H 15/00* (2018.01); *G16H 20/00* (2018.01)

(56) References Cited

U.S. PATENT DOCUMENTS

| | | | | |
|---|---|---|---|---|
| 8,566,738 | B2 * | 10/2013 | Van Vlimmeren | G16H 10/60 715/772 |
| 8,928,606 | B1 * | 1/2015 | Khafizova | G06F 3/04842 345/173 |
| 9,968,251 | B2 | 5/2018 | Kurzke et al. | |
| 10,402,537 | B2 * | 9/2019 | Segawa | G16H 10/60 |
| 2006/0265249 | A1 | 11/2006 | Follis et al. | |
| 2008/0208631 | A1 * | 8/2008 | Morita | G16H 40/60 705/3 |
| 2008/0244453 | A1 * | 10/2008 | Cafer | G06F 3/04817 715/835 |
| 2009/0054755 | A1 * | 2/2009 | Shiibashi | G16H 15/00 600/407 |
| 2009/0222286 | A1 | 9/2009 | Elsholz | |
| 2011/0286647 | A1 * | 11/2011 | Cao | G16H 30/20 382/131 |
| 2012/0131507 | A1 * | 5/2012 | Sparandara | G16H 10/60 715/833 |
| 2013/0179178 | A1 * | 7/2013 | Vemireddy | G06Q 10/00 705/2 |
| 2013/0290024 | A1 * | 10/2013 | Kawanaka | G16H 10/60 705/3 |
| 2014/0019915 | A1 * | 1/2014 | Livermore | G06F 16/904 715/838 |
| 2015/0269323 | A1 * | 9/2015 | Ginsburg | G16H 10/60 705/3 |
| 2017/0068780 | A1 * | 3/2017 | Dobrean | G16H 30/40 |
| 2017/0185744 | A1 * | 6/2017 | Okabe | G16H 50/20 |
| 2017/0199189 | A1 * | 7/2017 | Wade | G16H 50/30 |
| 2018/0292978 | A1 * | 10/2018 | Davies | G06F 3/04845 |
| 2021/0183487 | A1 * | 6/2021 | Teodoro | G16H 40/60 |

* cited by examiner

| Record | Patient ID | Patient Name | Exam Date | Exam Time | Exam Modality | Anatomy Examined | Physician Notes | Patient Information | Exam Data |
|---|---|---|---|---|---|---|---|---|---|
| 1 | 1234 | John Smith | 8/18/2001 | 8:58 AM | B-scan | Right Eye | Lower right quadrant... | 35 YO Male... | Machine calibrated... |
| 2 | 1234 | John Smith | 10/18/2001 | 10:35 AM | B-scan | Right Eye | Slight separation... | 35 YO Male... | Machine calibrated... |
| 3 | 5039 | Jane Smith | 5/21/2005 | 9:25 AM | Spectralis | Left Eye | Retina appears normal... | 35 YO Female... | Machine configuration... |
| 4 | 5309 | Jane Smith | 7/5/2013 | 3:02 PM | Spectralis | Left Eye | Change in upper... | 35 YO Female... | Machine configuration... |
| 5 | 1234 | John Smith | 11/01/2002 | 11:25 AM | B-scan | Right Eye | Separation Increasing... | 35 YO Male... | Machine calibrated... |
| ... | | | | | | | | | |
| 10005 | 5309 | Jane Smith | 1/22/2015 | 10:47 AM | Spectralis | Right Eye | No progression | 35 YO Female... | Machine configuration... |
| 10006 | 101 | Bill Johnson | 09/23/2015 | 4:02 PM | Kowa | Left Eye | Macular... | 57 YO Male... | Interlocks set to... |

FIG. 9

METHOD AND APPARATUS FOR A TREATMENT TIMELINE USER INTERFACE

CROSS-REFERENCE TO RELATED APPLICATIONS

This application claims the benefit of U.S. Provisional Application No. 62/750,612 filed Oct. 25, 2018, which is incorporated herein by reference.

FIELD OF THE INVENTION

The present disclosure relates generally to medical record systems, and more particularly to a system and method for generating and displaying a treatment timeline user interface.

BACKGROUND

Current medical record systems take the form of lists or tables of fragmented data points, requiring a physician to do a lot of list scanning and mental arithmetic to gain insight into each patient's condition. Patient records are often in the form of a group of documents, such as patient identification information and exam results, placed in a physical folder. It is time consuming for a physician to review the contents of the folder in order to make a diagnosis of a condition or assess the health of a patient due to the documents being out of order or not arranged in a manner conducive to a particular review required by the physician. Even when documents are stored electronically, the documents are generally not arranged or displayed in a manner that allows the physician to easily and quickly assess a patient's condition.

SUMMARY

A method and apparatus for a treatment timeline user interface includes maintaining a patient database of patient information. The patient information includes patient identification information and examination data associated with patients. A treatment timeline of a patient is generated based on patient information in response to receiving a patient identifier. An updated treatment timeline is generated in response to a request to modify the treatment timeline and the updated treatment timeline is displayed. Examination data is retrieved from the patient database based on a particular patient identifier and the treatment timeline is generated based on that data. In one embodiment, the treatment timeline comprises a plurality of active and inactive elements. The treatment timeline includes a time span focus selector that changes a time span of the treatment timeline in response to selection by a user. The treatment timeline comprises a time span focus toolbar that is displayed in response to the treatment timeline displaying less than the total number of years of exam history associated with the particular patient identifier. The treatment timeline can comprise a modality label identifying a modality that was used to examine a patient associated with the particular patient identifier. In one embodiment, the treatment timeline comprises a plurality of individual exam markers arranged by time of exam along a horizontal axis and arranged by exam modality along a vertical axis. The individual exam markers represent examination data associated with a respective individual exam marker and can be selected to display a thumbnail of the related examination data.

BRIEF DESCRIPTION OF THE DRAWINGS

FIG. 9 depicts a patient table of a patient record database comprising patient records according to an embodiment.

DETAILED DESCRIPTION

The present disclosure describes a system and method for generating and displaying a treatment timeline user interface that replaces the disjointed records of medical record systems with a single, consolidated, infographic-style overview of the patient's entire exam history in a manner that makes it quick and easy for the physician to grasp the history and context of a patient's previous care.

The context for a situation can be understood by answering basic questions including: who, what, when, where, how, and why. In the Ophthalmology treatment process the answers to who and where are already known when the physician meets the patient. The treatment timeline user interface (UI) described herein visualizes the answers to what has happened, how it was done, when it was done, and how much time has passed between actions. It does this in a manner that makes it easy for the physician to deduce whether the patient's treatment has been effectively pursued to date, and most important, reveal or remind the physician why the physician proceeded in this manner.

In one embodiment, patient information is maintained in a patient record database comprising a patient table. The patient table includes patient records which identify information pertaining to a physician's past decisions. This information can include what exams were performed, when the exams were performed, the number of exams of each modality (e.g., a type of examination) that were performed, whether a modality was added to the patient's normal protocol, whether the span of time that elapsed between two exams of the same modality is indicative of a change in rate of a disease's progression, and whether a past exam was repeated so soon by a previous physician that a current physician should suspect something was found that required re-checking.

The patient record can also identify information pertaining to a patient's past performance. The patient record can include information pertaining to whether a patient's approach to their own care is supportive of the prescribed treatments, whether there were any exams that should have been done on a regular basis that were missed entirely, and whether there are any seasonal, holiday, or cultural factors that could be impacting a patient's results.

Figure 1:
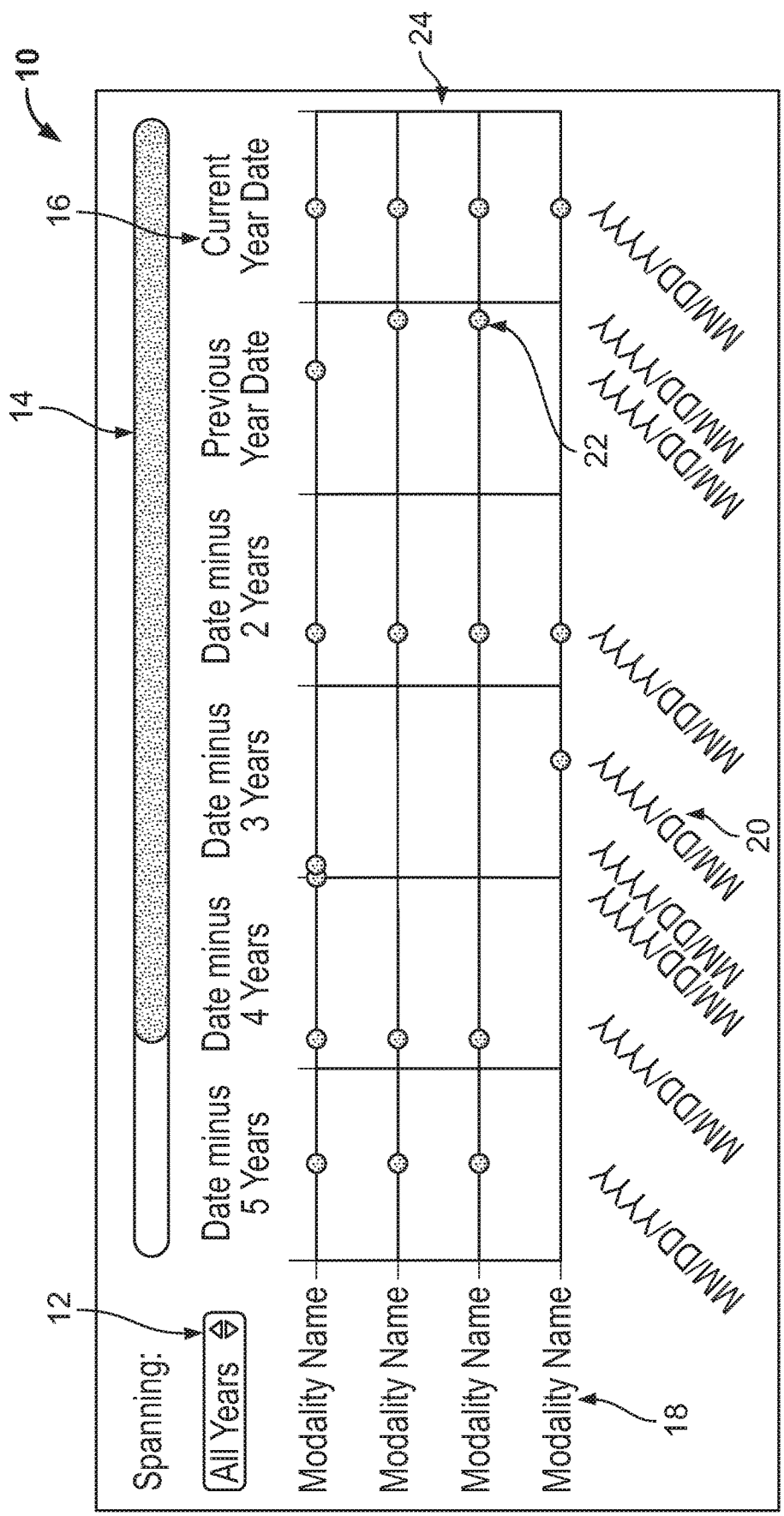
FIG. 1 depicts a treatment timeline user interface according to an embodiment.

FIG. 1 shows treatment timeline user interface 10 which is displayed using a computer (e.g., computer 1002 shown in FIG. 10) according to one embodiment. Treatment timeline user interface 10 includes various active and inactive elements displayed to a user (e.g., a physician). Active elements can be used to change the information that is displayed on the treatment timeline user interface 10. Active elements, in one embodiment, can be selected by hovering over the element with a pointer and clicking a button. Inactive elements are display only and cannot be selected or clicked to change the information displayed.

Figures 3A, 3B:
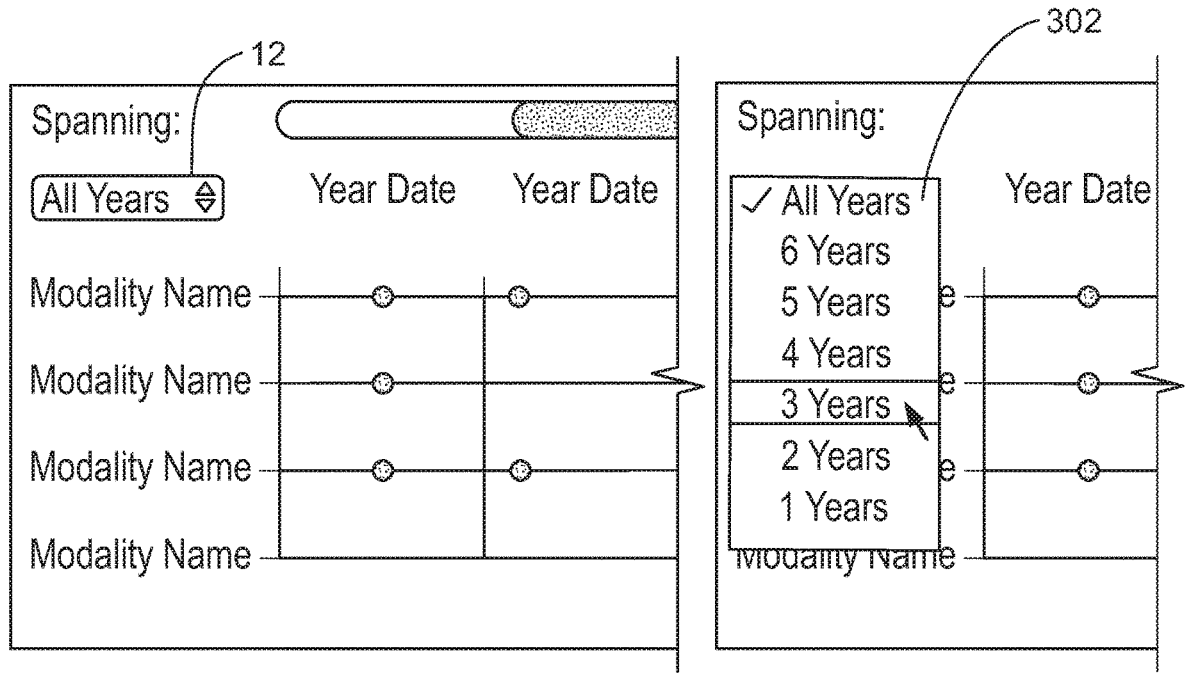
FIG. 3A depicts a portion of a treatment timeline user interface according to an embodiment.
FIG. 3B depicts a portion of a treatment timeline user interface including a pop up window associated with a time span focus selector according to an embodiment.

Time span focus selector 12 allows a user to focus on less than the total number of years that encompass the patient's total exam history. Time span focus selector 12 can be used to narrow the span of years that are displayed to a user. In one embodiment, a default value for the time span focus selector 12 is the entire span of the patient's exam history, or 5 years, depending on a user's preferences. FIG. 3A depicts a portion of treatment timeline user interface 10 prior to time span focus selector 12 being selected (e.g. clicked on). FIG. 3B depicts time span focus selector pop up window 302 which appears in response to time span focus selector 12 being selected. A user can then select a particular span for viewing by selecting one of the options displayed in time span focus selector pop up window 302.

Returning to FIG. 1, time span focus toolbar 14 is a scroll bar that allows the user to change a time span to display information associated with earlier or later dates and/or times than the dates and/or times currently displayed. In one embodiment, time span focus toolbar 14 is displayed when a user is reviewing less than the total number of years that encompass the patient's total exam history.

Year label 16 identifies a year associated with information displayed below the label. In one embodiment, each year is comprised of four quarters but other divisions can be used as well. In one embodiment, year label 16 is an inactive element that cannot be selected and/or clicked. Year labels are displayed along a horizontal axis of time line 24.

Modality label 18 identifies a modality that was used to examine the patient associated with the information displayed. In one embodiment, each modality employed to examine the patient is identified on a vertical axis of time line 24. In embodiments of treatment timeline user interface 10 used to review ophthalmic treatment of a patient, it is noted that patients are not often examined with more than 5 modalities. However, any number of modality labels can be displayed by expanding treatment timeline user interface 10 vertically in order to accommodate the number of modalities to be displayed. Modality label 18 can be selected by hovering over modality label 18 and clicking on it. Selecting a particular modality label 18 clears the display and replaces it with a thumbnail gallery of images from the selected modality for all exam dates. Each of the displayed thumbnails can be selected to view a larger image of the respective thumbnail image. In one embodiment, a clickable icon is displayed along with the thumbnail images which a user can click to return the view shown in FIG. 1. In one embodiment, each modality label 18 is an active link to all exams performed for the respective modality.

Exam date label 20 identifies the date on which a patient associated with treatment timeline user interface 10 was examined. Date labels are displayed along a horizontal axis of time line 24. Selecting a particular exam date label 20 clears the display and replaces it with a thumbnail gallery of images for all the modalities associated with the date identified by the selected exam date label. In embodiments of treatment timeline user interface 10 used to review ophthalmic treatment of a patient, it is noted that patients are not often examined more than 3 times per year. If the number of exam dates causes the associated exam date labels to overlap, time span focus selector 12 can be used to narrow the time span displayed in order to display each exam date label without overlapping neighboring labels. As the time span selected is narrowed, the exam date labels become more widely spread across the same display distance. In one embodiment, each exam date label 20 is an active link to all of the exams performed on the respective date of all modalities. Clicking on exam date label 20 causes the display of thumbnails in a thumbnail display area. The thumbnails displayed are associated with the exams performed on the respective date.

Figure 4:
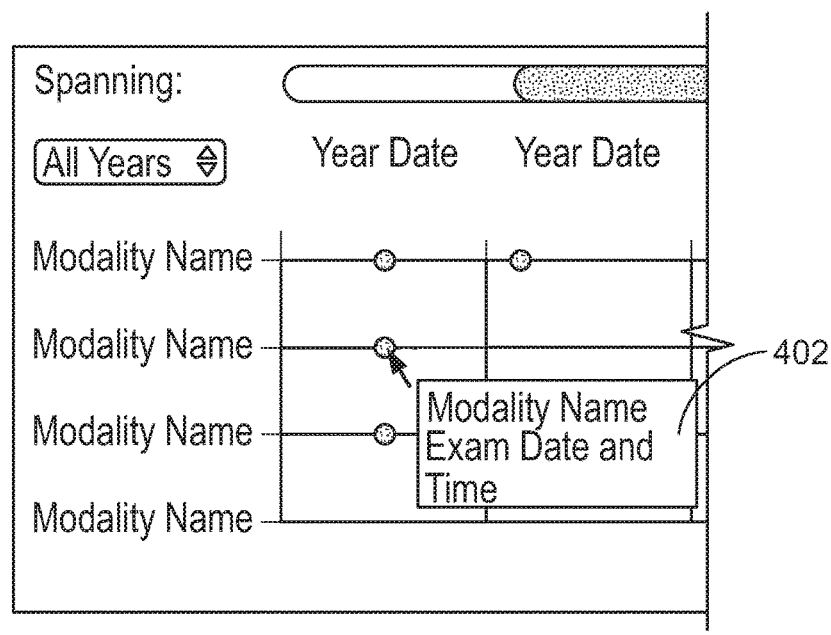
FIG. 4 depicts a flyout displayed in response to a user hovering a pointer over an exam marker according to an embodiment.

Individual exam marker 22 is a clickable icon (e.g., a dot that can be selected by hovering over the dot and clicking) located at an intersection of a modality row and a date of an exam. Hovering a pointer over individual exam marker 22 reveals a small flyout (e.g., a popup window) that indicates information associated with exams represented by the marker. FIG. 4 depicts flyout 402 which appears after a pointer is hovered over an individual exam marker.

As shown in FIG. 4, in one embodiment, modality name and exam date and time are displayed in flyout 402. Flyout 402 can additionally or alternatively display an indication a total number of images capture during the associated exam, an indication of a number of images that have been favorited by physicians, and a number of images that have been shared by physicians. This information can help a physician quickly gauge the likelihood that this particular exam has information important to evaluating the associated patient's condition without having to re-open the collection of images to re-evaluate them every time.

Figure 5:
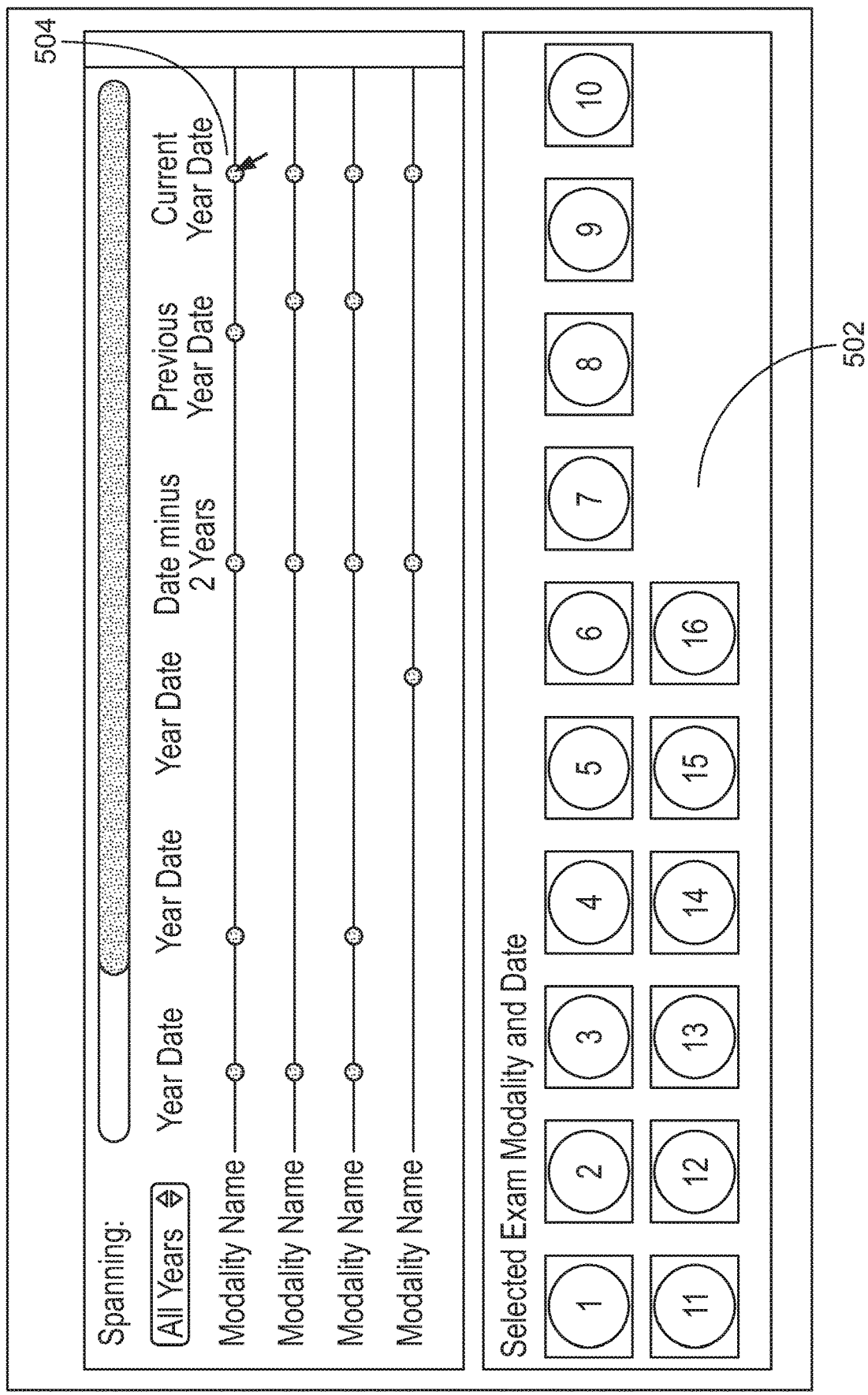
FIG. 5 depicts a display of set of thumbnail images according to an embodiment.

Returning to FIG. 1, in one embodiment, a user can click on each individual exam marker 22 to view information associated with the selected marker. In one embodiment, clicking on a single exam marker triggers the appearance of image thumbnails for that exam in the viewing area. The number of thumbnails shown depends on the size of each thumbnail and a size of the viewing area. Thumbnails that cannot be shown can be viewed by manipulation of a scroll bar described in detail below. In situations where a single exam for a single modality is selected for which there is only a single image or file, one image appears full size in the viewing area. In one embodiment, clicking the same individual exam marker 22 again triggers the disappearance of the image thumbnails. FIG. 5 depicts thumbnails 502 which appear in response to a user clicking exam marker 504.

In one embodiment, clicking a second exam marker causes the image thumbnails from the first exam marker to move aside to fill only a half of the thumbnail display area. Thumbnails associated with the second exam marker are displayed in the half of the thumbnail display area not populated with images associated with the first exam marker.

Figure 6:
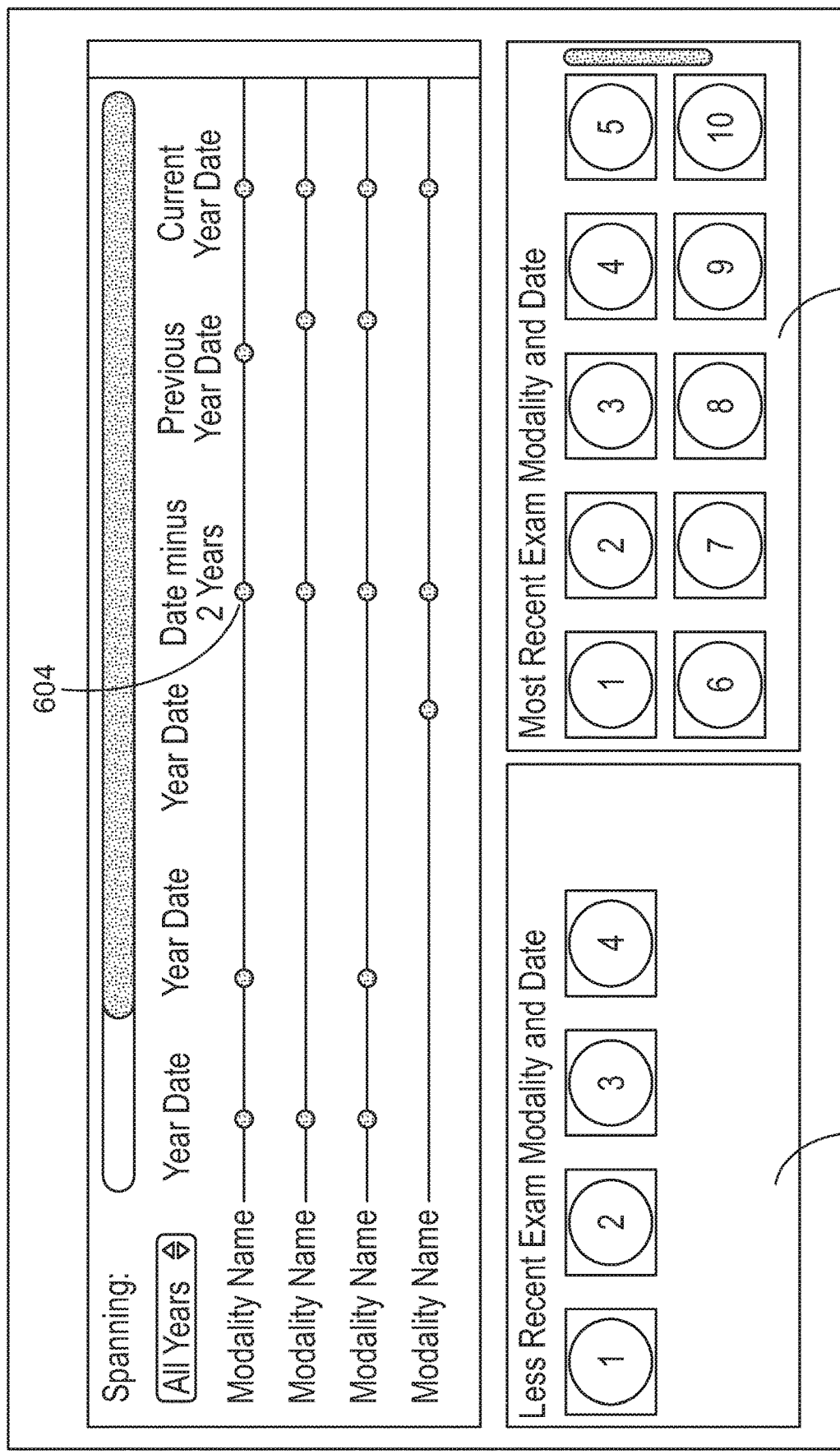
FIG. 6 depicts a display of two sets of thumbnail images according to an embodiment.

FIG. 6 depicts thumbnails 502 and thumbnails 602 which are located adjacent to one another. Thumbnails 502 and thumbnails 602 are displayed adjacent to each other in response to a user clicking exam marker 604 after having previously clicked on exam marker 504.

Figure 7:
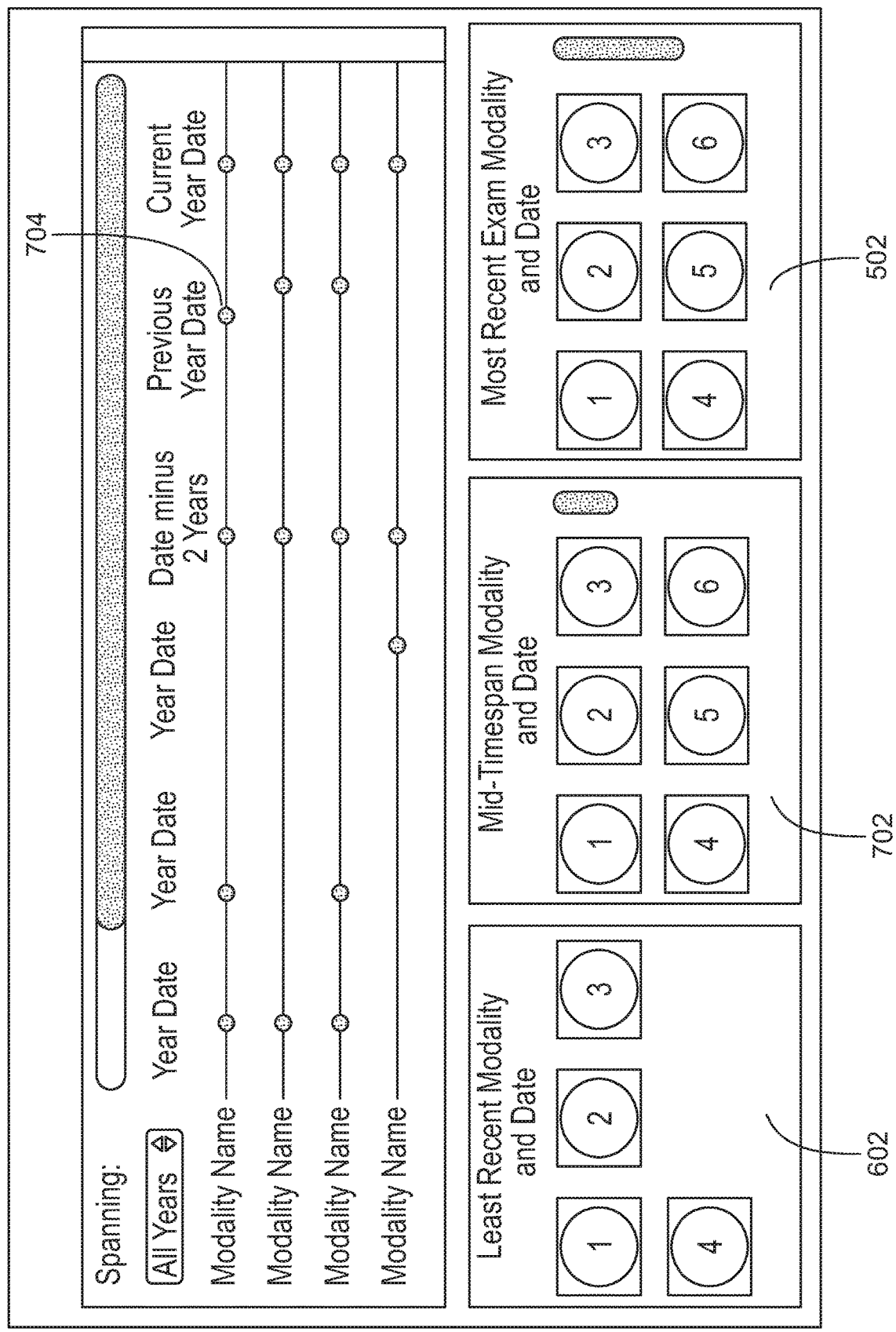
FIG. 7 depicts a display of three sets of thumbnail images according to an embodiment.

If a third exam marker is selected, the thumbnail display area will display images associated with the third exam marker in a third portion of the thumbnail display area. FIG. 7 depicts thumbnails 502, thumbnails 602, and thumbnails 702 displayed adjacent to one another. Thumbnails 502, thumbnails 602, and 702 are displayed adjacent to each other in response to a user clicking exam marker 704 after having previously clicked on exam marker 504 and exam marker 604.

Clicking a fourth exam marker causes the thumbnail display area to display images associated with each selected exam marker in a fourth portion of the thumbnail display area. In one embodiment, based on the number of exam markers selected, the thumbnail display area displays images associated with each respective exam in one of multiple portions of the thumbnail display area. If the number of exam markers and associated thumbnail images to be displayed exceeds the number of thumbnail images that can be displayed in the thumbnail display area, then the thumbnail display area is displayed with a scroll bar that can be used to scroll the displayed images left or right to display any adjacent sets of images in the thumbnail display area.

It should be noted that clicking more than one exam marker associated with the same date aids in a physician's diagnosis of the patient's condition. This can be particularly effective in combination with filtering controls for the thumbnail display area which allow a user (e.g., the physician) to declutter the collection of thumbnail images displayed in the thumbnail display area that are of the opposite eye of the eye desired to be viewed, flawed images, or images that were otherwise not considered to be important in the past.

Clicking more than one exam marker of the same modality assists the physician's evaluation of the rate of change for a given condition. This is similar to a historic compare function which allows a user to view large format images but also produces galleries of thumbnails instead of a second large format image of the same eye.

Figure 2:
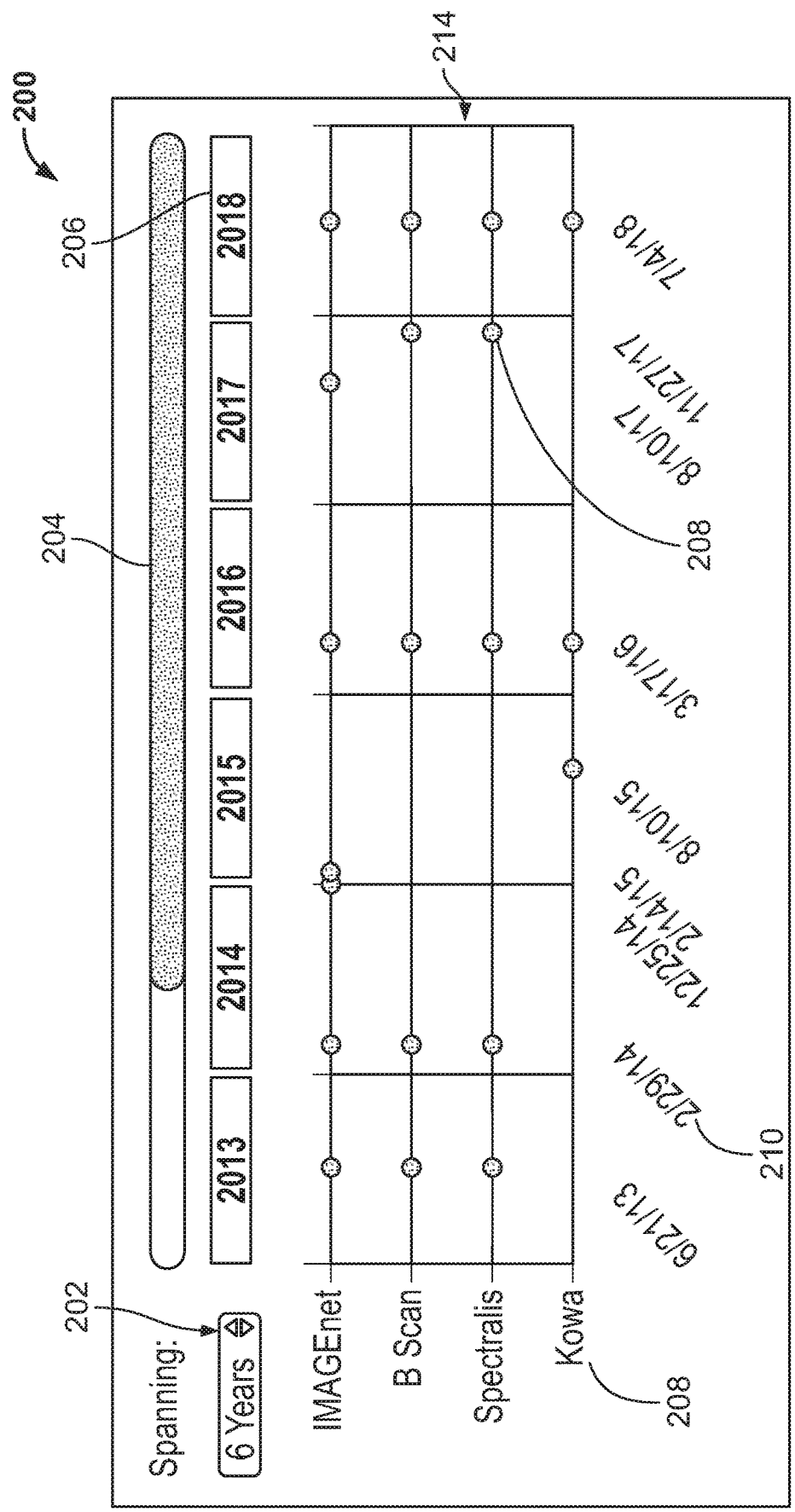
FIG. 2 depicts a treatment timeline user interface for a specific patient according to one embodiment.

FIG. 2 depicts treatment timeline user interface 200 which is similar to treatment timeline user interface 10 but is for a specific patient (i.e., use of the timeline to display patient information). Similar to treatment timeline user interface 10, treatment timeline user interface 200 depicts time span focus selector 202, time span focus toolbar 204, year label 206, modality label 208, exam date label 210, and individual exam marker 212, each of which displays information relevant to a patient and examinations that have been performed on the patient. In treatment timeline user interface 200, the associated patient has an exam history that spans 8 years. During the most recent 6 years of those 8 years, the patient has visited a physician's office 9 times (i.e., 9 different examination dates are identified by nine different exam date labels 210). This patient has also visited a few times previous to 2013 but those visits do not fall within the span of time displayed in treatment timeline user interface 200 based on the selection of 6 years as shown in time span focus selector 202. The patient information identified in treatment timeline user interface 200 displays information from exams spanning 6 years including 7 sets of IMAGEnet images, 5 sets of B-scan images, 5 sets of Spectralis images, and 3 sets of Kowa images. Time span focus toolbar 204 allows the user to drag the selected span of years displayed across the patient's total span of exam history. As shown in FIG. 2, the patient has an eight year history so time span focus toolbar 204 shows a slider three-quarters of the total width of time span focus toolbar 204.

Figure 8:
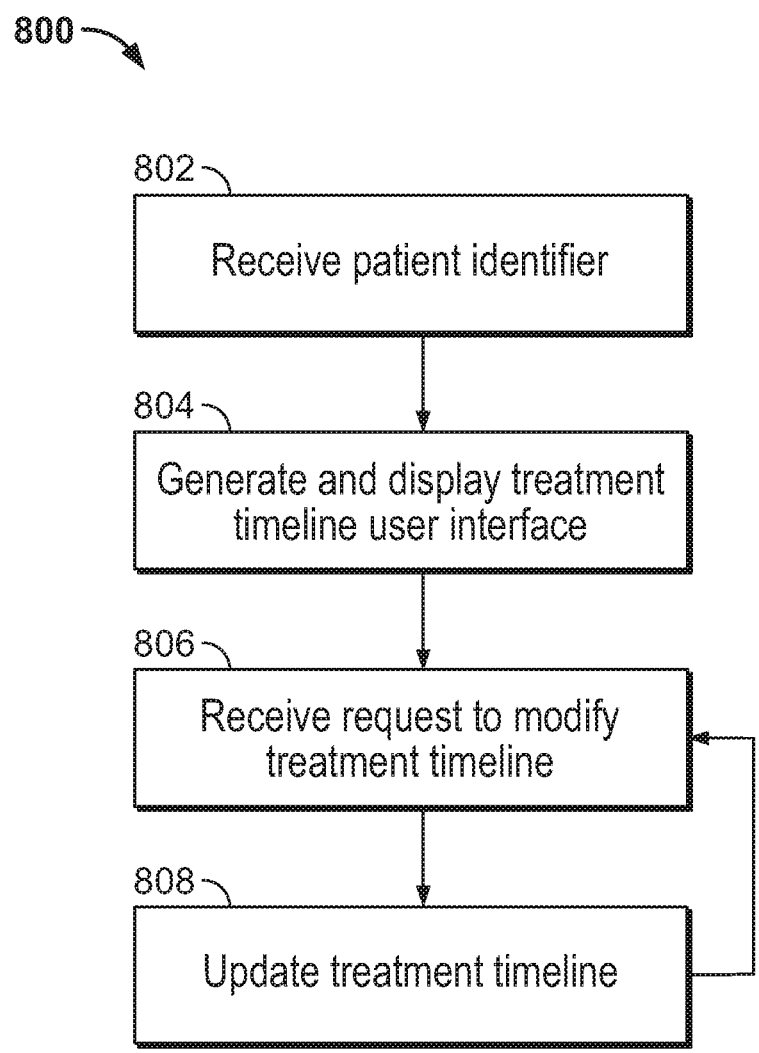
FIG. 8 depicts a flowchart of a method according to an embodiment.

FIG. 8 depicts a flowchart of a method 300 for a displaying a treatment timeline user interface using a computer storing a patient information in a patient record database. The patient database is maintained by receiving and cataloging patient information such as patient identifying information and patient exam information as previously described in connection with FIGS. 1 through 7. Patient exam information can include both text and images associated with exams that have been performed on the patient. At step 802, a patient identifier is received. A patient identifier, in one embodiment, is a unique identifier (e.g., a numeric or alphanumeric) associated with a patient. At step 804, a treatment timeline user interface (such as treatment timeline interface 200 shown in FIG. 2) is generated and displayed to a user. At step 806 input is received requesting modification of the treatment timeline user interface. Input can be, for example, a user selecting an exam marker, moving a scroll bar, or any interaction with an active element that is displayed. At step 808, the treatment timeline user interface is updated in response to the input received in step 806. Steps 806 and 808 can be repeated as long as additional input is received from a user.

FIG. 9 depicts a patient table 900 of a patient record database according to an embodiment. Patient table 900 comprises patient records 902-914 each of which contain information regarding a patient and a particular examination. Each record 902-914 is associated with an identifier located in the column titled Record 920 which uniquely identifies the record. A unique patient identifier is located in the column titled Patient ID 922 column. A date and time of a particular examination are respectively stored in the columns titled Exam Date 926 and Exam Time 928. A modality of an exam is identified in the column titled Exam Modality 930. An identification of the particular part of a patient's anatomy is identified in the column titled Anatomy Examined 932. Notes concerning a particular exam are stored in the column titled Physician Notes 934. Information concerning a particular patient is stored in the column titled Patient Information 936. Exam data, in one embodiment, is the output of a machine used for examination and is stored in the column titled Exam Data 938. It should be noted that records can include more or less columns based on information a user, such as a physician, would like to record.

Figure 10:
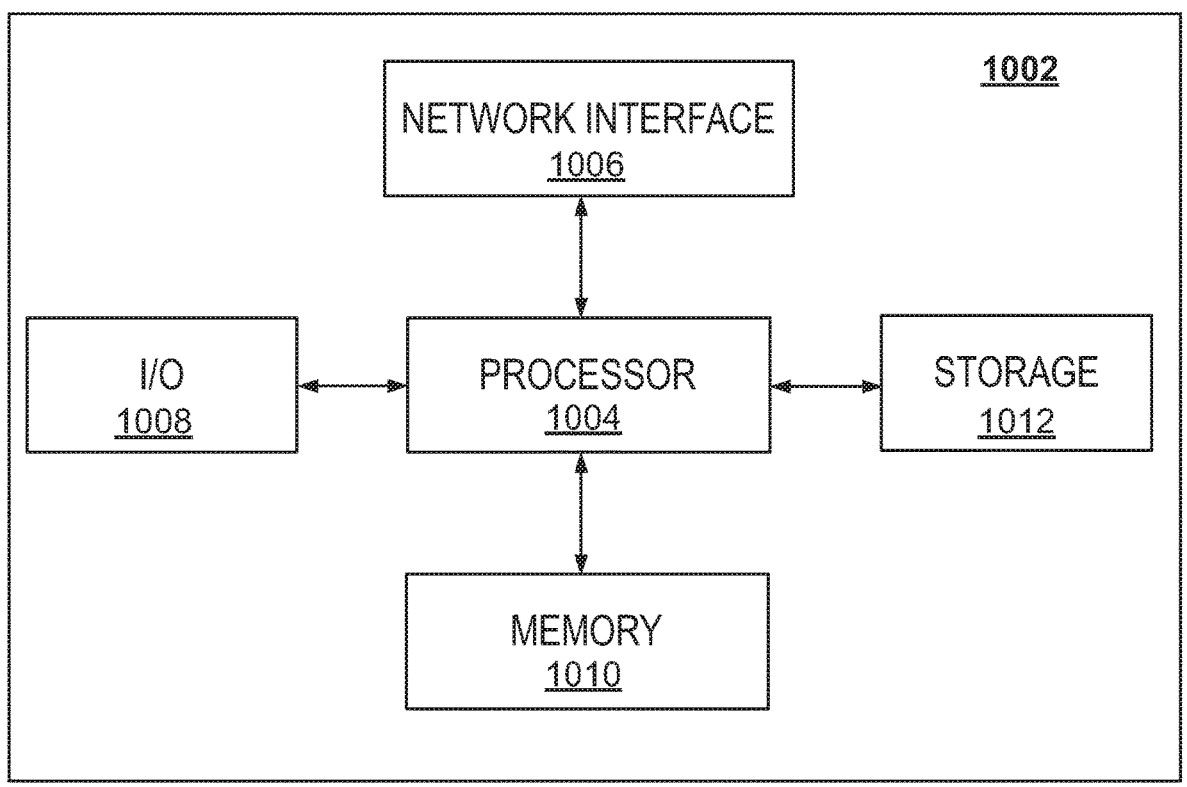
FIG. 10 depicts a block diagram of a computer used to generate and display a treatment timeline according to an embodiment.

Treatment timeline user interface 200 can be implemented using a computer with a display. For example, treatment timeline user interface 200 can be implemented using a desktop or tablet. A high-level block diagram of such a computer is illustrated in FIG. 10. Computer 1002 contains a processor 1004 which controls the overall operation of the computer 1002 by executing computer program instructions which define such operation. The computer program instructions may be stored in a storage device 1012, or other computer readable medium (e.g., magnetic disk, CD ROM, etc.), and loaded into memory 1010 when execution of the computer program instructions is desired. Thus, the method steps of FIG. 8 can be defined by the computer program instructions stored in the memory 1010 and/or storage 1012 and controlled by the processor 1004 executing the computer program instructions. For example, the computer program instructions can be implemented as computer executable code programmed by one skilled in the art to perform an algorithm defined by the method steps of FIG. 8. Accordingly, by executing the computer program instructions, the processor 1004 executes an algorithm defined by the method steps of FIG. 8. The computer 1002 also includes one or more network interfaces 1006 for communicating with other devices via a network. The computer 1002 also includes input/output devices 1008 that enable user interaction with the computer 1002 (e.g., display, keyboard, mouse, speakers, buttons, etc.) One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the inventive concept disclosed herein is not to be determined from the Detailed Description, but rather from the claims as interpreted according to the full breadth permitted by the patent laws. It is to be understood that the embodiments shown and described herein are only illustrative of the principles of the inventive concept and that various modifications may be implemented by those skilled in the art without departing from the scope and spirit of the inventive concept. Those skilled in the art could implement various other feature combinations without departing from the scope and spirit of the inventive concept.

The invention claimed is:

1. A method comprising:
   maintaining a patient database of patient information, the patient information comprising a plurality of patient identifiers and associated examination data;
   receiving a particular patient identifier;
   generating a treatment timeline of a patient based on patient information associated with the particular patient identifier, the treatment timeline comprising:
      a plurality of individual exam markers arranged by a date and a time of a respective exam along a first axis and arranged by exam modality along a second axis; and
      a modality label identifying a modality that was used to examine a patient; and
      a date label identifying a date associated with the respective exam;
   displaying the treatment timeline; and
   displaying multiple thumbnails of examination data in response to selection of multiple ones of the plurality of individual exam markers.

2. The method of claim 1, further comprising:
   receiving a request to modify the treatment timeline;
   updating the treatment timeline based on the request to generate an updated treatment timeline; and
   displaying the updated treatment timeline.

3. The method of claim 2, wherein the request to modify the treatment timeline comprises input selecting a modality label and the updated treatment timeline comprises a display of a thumbnails of examination data pertaining to a modality identified by the modality label.

4. The method of claim 1, wherein each of the plurality of individual exam markers represents examination data associated with a patient, a modality, and a date and time.

5. The method of claim 4, wherein examination data is displayed in response to selection of one of the plurality of individual exam markers.

6. The method of claim 4, wherein a thumbnail of examination data is displayed in response to selection of one of the plurality of individual exam markers.

7. An apparatus comprising:
   a processor; and
   a memory to store computer program instructions, the computer program instructions when executed on the processor cause the processor to perform operations comprising:
      maintaining a patient database of patient information, the patient information comprising a plurality of patient identifiers and associated examination data;
      receiving a particular patient identifier;
      generating a treatment timeline of a patient based on patient information associated with the particular patient identifier, the treatment timeline comprising:
         a plurality of individual exam markers arranged by a date and a time of a respective exam along a first axis and arranged by exam modality along a second axis;
         a modality label identifying a modality that was used to examine a patient; and
         a date label identifying a date associated with the respective exam;
      displaying the treatment timeline; and
      displaying multiple thumbnails of examination data in response to selection of multiple ones of the plurality of individual exam markers.

8. The apparatus of claim 7, the operations further comprising:
   receiving a request to modify the treatment timeline;
   updating the treatment timeline based on the request to generate an updated treatment timeline; and
   displaying the updated treatment timeline.

9. The apparatus of claim 8, wherein the request to modify the treatment timeline comprises input selecting a modality label and the updated treatment timeline comprises a display of a thumbnails of examination data pertaining to a modality identified by the modality label.

10. The apparatus of claim 7, wherein each of the plurality of individual exam markers represents examination data associated with a patient, a modality, and a date and time.

11. The apparatus of claim 10, wherein examination data is displayed in response to selection of one of the plurality of individual exam markers.

12. The apparatus of claim 10, wherein a thumbnail of examination data is displayed in response to selection of one of the plurality of individual exam markers.

13. A non-transitory computer readable medium storing computer program instructions, which, when executed on a processor, cause the processor to perform operations comprising:
   maintaining a patient database of patient information, the patient information comprising a plurality of patient identifiers and associated examination data;
   receiving a particular patient identifier;
   generating a treatment timeline of a patient based on patient information associated with the particular patient identifier, the treatment timeline comprising:
      a plurality of individual exam markers arranged by a date and a time of a respective exam along a first axis and arranged by exam modality along a second axis; and
      a modality label identifying a modality that was used to examine a patient; and
      a date label identifying a date associated with the respective exam;
   displaying the treatment timeline; and
   displaying multiple thumbnails of examination data in response to selection of multiple ones of the plurality of individual exam markers.

14. The non-transitory computer readable medium of claim 13, the operations further comprising:
   receiving a request to modify the treatment timeline;
   updating the treatment timeline based on the request to generate an updated treatment timeline; and
   displaying the updated treatment timeline.

15. The non-transitory computer readable medium of claim 13, wherein each of the plurality of individual exam markers represents examination data associated with a patient, a modality, and a date and time.

16. The non-transitory computer readable medium of claim 15, wherein examination data is displayed in response to selection of one of the plurality of individual exam markers.

17. The non-transitory computer readable medium of claim 15, wherein a thumbnail of examination data is displayed in response to selection of one of the plurality of individual exam markers.

\* \* \* \* \*